(12) United States Patent
Toyoda et al.

(10) Patent No.: US 9,877,693 B2
(45) Date of Patent: Jan. 30, 2018

(54) X-RAY IMAGING APPARATUS AND X-RAY IMAGING METHOD

(71) Applicant: SHIMADZU CORPORATION, Nakagyo-ku, Kyoto-shi (JP)

(72) Inventors: Toshihide Toyoda, Kyoto (JP); Naohiko Wakayama, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 198 days.

(21) Appl. No.: 15/021,884

(22) PCT Filed: Sep. 24, 2013

(86) PCT No.: PCT/JP2013/075718
§ 371 (c)(1),
(2) Date: Mar. 14, 2016

(87) PCT Pub. No.: WO2015/045005
PCT Pub. Date: Apr. 2, 2015

(65) Prior Publication Data
US 2016/0228086 A1 Aug. 11, 2016

(51) Int. Cl.
*A61B 6/00* (2006.01)

(52) U.S. Cl.
CPC ............ *A61B 6/5241* (2013.01); *A61B 6/463* (2013.01)

(58) Field of Classification Search
CPC .............................. A61B 6/463; A61B 6/5241
See application file for complete search history.

(56) References Cited

U.S. PATENT DOCUMENTS

2010/0020929 A1* 1/2010 Akahori ............... A61B 6/4233
378/62

FOREIGN PATENT DOCUMENTS

| JP | 2013-39197 | | 2/2013 |
|---|---|---|---|
| JP | 2013039197 A | * | 2/2013 |
| JP | 2015-538658 | | 6/2013 |
| JP | 2013-154146 | | 8/2013 |

OTHER PUBLICATIONS

JP 2015-538658, Office Action dated Feb. 2, 2016, 3 pages—Japanese; 3 pages—English.
PCT/JP2013/075718, International Search Report dated Oct. 22, 2013, 1 page—English, 2 pages—Japanese.

* cited by examiner

*Primary Examiner* — Mark R Gaworecki
(74) *Attorney, Agent, or Firm* — Andrew F. Young, Esq.; Lackenbach Siegel, LLP

(57) ABSTRACT

An X-ray imaging apparatus has an X-ray tube that irradiates an X-ray to a subject, an flat panel detector (FPD) that takes an X-ray image on the basis of the X-ray transmitted through the subject, a real-time image synthesis element that synthesizes an image by connecting in turn an image of a plurality of strip-shape X-ray images concurrently taken while letting the X-ray tube and the FPD move relative with respect to the subject, and a real-time image monitor that displays an intermediate image taken by the FPD and is synthesized in turn by the real-time image synthesis element.

11 Claims, 4 Drawing Sheets

X-RAY IMAGING APPARATUS AND X-RAY IMAGING METHOD

CROSS REFERENCE TO RELATED APPLICATIONS

This application relates to and is a § 371 national phase of Ser. PCT/JP2013/075718 filed Sep. 24, 2013, the entire contents of which are incorporated herein by reference.

BACKGROUND OF THE INVENTION

Technical Field

The present invention relates to an X-ray imaging apparatus and an X-ray imaging method, and more particularly, relates to an X-ray imaging apparatus and an X-ray imaging method that synthesize an image from a plurality of strip-shape X-ray images.

Background Art

Conventionally, it is known that there is an X-ray imaging apparatus to synthesize an image from a plurality of strip-shape X-ray images. Such an X-ray imaging apparatus is disclosed in Japanese Patent Laying-Open No. 2012-254160, for example.

The X-ray imaging apparatus disclosed in the aforementioned Japanese Patent Laying-Open No. 2012-254160 includes an X-ray tube bulb to irradiate an X-ray to a subject and an X-ray detector to take X-ray images on the basis of the X-ray transmitted through the subject. Such an X-ray imaging apparatus is configured to squeeze the region irradiated with the X-ray into a slit manner and so as to take a plurality of strip-shape X-ray images. Further, such an X-ray imaging apparatus is configured to synthesize one image by connecting the plurality of strip-shape X-ray images following taking all strip-shape X-ray images. In such a conventional X-ray imaging apparatus, the taken strip-shape X-ray images are configured to be individually displayed one by one every imaging.

PRIOR ART

Patent Document 1: Japanese Patent Laying-Open No. 2012-254160

ASPECTS AND SUMMARY OF THE INVENTION

Problem to be Solved by the Invention

In the X-ray imaging apparatus according to the aforementioned Japanese Patent Laying-Open No. 2012-254160, however, since the taken strip-shape X-ray images are individually displayed one by one every imaging, it is a substantial problem that it is difficult to recognize which parts of the subject are imaged.

The present invention has been proposed in order to solve the aforementioned problem, and an object of the present invention is to provide an X-ray imaging apparatus and an X-ray imaging method that can easily recognize which parts of a subject correspond to the taken strip-shape X-ray images.

Means for Solving the Problem

In order to attain the aforementioned object, an X-ray imaging apparatus according to a first aspect of the present invention comprises an X-ray irradiation element that irradiates an X-ray to a subject, an X-ray imaging element that takes an X-ray image on the basis of the X-ray transmitted through the subject, an image synthesis element that synthesize an image by connecting in turn the plurality of strip-shape X-ray images that are concurrently-taken while letting the X-ray irradiation element and the X-ray imaging element relative-move with respect to the subject, and a first display element that displays a intermediate image taken by the X-ray imaging element and synthesized in turn by the image synthesis element.

In the X-ray imaging apparatus according to the first aspect of the present invention, as hereinabove described, the image synthesis element that synthesizes the image by connecting in turn the plurality of strip-shape X-ray images concurrently-taken while letting the X-ray irradiation element and the X-ray imaging element relative-move with respect to the test subject and the first display element that displays the intermediate image taken by the X-ray imaging element and synthesizes in turn by the image synthesis element are so provided that which parts of the subject have been imaged in the taken strip-shape X-ray images can be easily recognized by the intermediate image in which the strip-shape X-ray images taken between the position of beginning of imaging and the current imaging position are synthesized. Further, since the image is synthesized halfway through the imaging, deviation can be recognized halfway through the imaging even when connected portions of the strip-shape X-ray images deviate due to movement of the subject and so forth. In this case, since the imaging can be held halfway, an increase in X-ray exposure to the subject resulting from a subsequent imaging can be suppressed.

Preferably in the aforementioned X-ray imaging apparatus according to the first aspect, the first display element is configured to display the intermediate image prior to the time when an X-ray for taking a next X-ray image is irradiated. When structuring the X-ray imaging apparatus in this manner, since the presence or absence of deviation in the connected portions of the X-ray images can be recognized prior to the time of the next imaging, the X-ray irradiation for taking the next X-ray image can be suspended by holding the imaging if there is deviation. Thus, an increase in X-ray exposure to the subject can be effectively suppressed.

Preferably in the aforementioned X-ray imaging apparatus according to the first aspect, the first display element is configured to display the intermediate image prior to the time when a next X-ray image is taken. When structuring the X-ray imaging apparatus in this manner, the taken X-ray images can be confirmed in real time by displaying the intermediate image every imaging of the strip-shape X-ray images. Further, the strip-shape X-ray images that have been taken by that time are connected and synthesized prior to the time when the next X-ray image is taken so that a processing burden can be reduced by inhibiting overlapping of imaging processing timing and synthesis processing timing.

Preferably, the aforementioned X-ray imaging apparatus according to the first aspect further comprises a diagnostic image processing element that performs image processing for diagnosis with respect to the image synthesized by the image synthesis element and a second display element that displays the image subjected to the image processing for diagnosis. According to structuring the X-ray imaging apparatus in this manner, not only which parts of a subject that correspond to the taken strip-shape X-ray images can be recognized by the intermediate image displayed on the first display, but also the subject can be diagnosed by the image, subjected to the image processing for diagnosis, displayed on the second display element.

Preferably in this case, the X-ray imaging apparatus further comprises a storage element that stores the image synthesized by the image synthesis element, and the diagnostic image processing element is configured to perform the image processing for diagnosis with respect to the image stored in the storage element. According to structuring the X-ray imaging apparatus in this manner, the image processing for diagnosis can be easily performed on the basis of the image, synthesized by the image synthesis element, stored in the storage element.

Preferably in the aforementioned structure providing the diagnostic image processing element, the image synthesis element is configured to synthesize a long image, of which longitudinal direction is a predetermined direction from the plurality of strip-shape X-ray images and the short-side direction is the predetermined direction, concurrently-taken while letting the X-ray irradiation element and the X-ray imaging element relative-move in the predetermined direction with respect to the subject. According to structuring the X-ray imaging apparatus in this manner, which parts of the long image, of which longitudinal direction is the predetermined direction, the plurality of strip-shape X-ray images and the short-side direction is the predetermined direction, correspond can be easily recognized by the intermediate image displayed on the first display element.

Preferably in the aforementioned X-ray imaging apparatus according to the first aspect, the image synthesis element is configured to post the user that a connected element deviates when the connected element of the synthesized image deviates on the basis of the synthesized intermediate image in turn. According to structuring the X-ray imaging apparatus in this manner, since the user can easily recognize the deviation halfway through the imaging, the imaging can be held by the user and an operation of retaking the deviated portions can be easily performed.

An X-ray imaging method according to a second aspect of the present invention comprises the steps of irradiating an X-ray to a subject, taking an X-ray image on the basis of the X-ray transmitted through the subject, synthesizing an image by connecting images of a plurality of strip-shape X-ray images concurrently-taken while letting an X-ray irradiation element and an X-ray imaging element relative-move with respect to the subject, and displaying an intermediate image synthesized by connecting in turn on a first display element.

In the X-ray imaging method according to the second aspect of the present invention, as hereinabove described, the steps of synthesizing the image by connecting in turn images of the plurality of strip-shape X-ray images concurrently taken while letting the X-ray irradiation element and the X-ray imaging element relative-move with respect to the subject and displaying the intermediate image synthesized by connecting in turn on the first display element are so provided that which parts of the subject correspond to the taken strip-shape X-ray images can be easily recognized by the intermediate image in which the strip-shape X-ray images between beginning position of imaging and a current imaging position are synthesized. Further, the image is synthesized halfway through the imaging so that a deviation can be recognized halfway through the imaging also when connected portions of the strip-shape X-ray images deviate due to e.g., movement of the subject. In this case, the imaging can be held halfway so that an increase in X-ray exposure to the subject resulting from a subsequent imaging can be suppressed.

Preferably in the aforementioned X-ray imaging method according to the second aspect, the step of displaying the intermediate image on the display element includes a step of displaying the intermediate image synthesized by connecting in turn prior to the time when an X-ray for taking a next X-ray image is irradiated. According to structuring the X-ray imaging method in this manner, the presence or absence of deviation in the connected portions of the X-ray images can be recognized prior to the time of the next imaging so that the X-ray irradiation for taking the next X-ray image can be suspended by holding the imaging when there is deviation. Thus, an increase in X-ray exposure to the subject can be effectively suppressed.

Preferably in the aforementioned X-ray imaging method according to the second aspect, the step of displaying the intermediate image on the display element includes a step of displaying the intermediate image synthesized by connecting in turn prior to the time when a next X-ray image is taken. According to structuring the X-ray imaging method in this manner, the taken X-ray images can be confirmed in real time by displaying the intermediate image every imaging of the strip-shape X-ray images. Further, the strip-shape X-ray images that have been taken by that time are connected and synthesized prior to the time when the next X-ray image is taken so that a processing burden can be reduced by inhibiting overlapping of an imaging processing timing and a synthesis processing timing.

Preferably, the aforementioned X-ray imaging method according to the second aspect further includes the steps of performing image processing for diagnosis with respect to the synthesized image and displaying the image subjected to the image processing for diagnosis on a second display element. According to structuring the X-ray imaging method in this manner, not only which parts of the subject have been imaged in the taken strip-shape X-ray images can be recognized by the intermediate image displayed on the first display element, but also the subject can be diagnosed by the image, subjected to the image processing for diagnosis, displayed on the second display element.

Effect of the Invention

As hereinabove described, which parts of the subject that have been imaged in the taken strip-shape X-ray images can be easily recognized according to the present invention.

DETAILED DESCRIPTION OF THE PREFERRED EMBODIMENTS

Embodiment of the present invention is now described on the basis of the drawings.

First, the overall structure of an X-ray imaging apparatus 100 according to Embodiment of the present invention is described with reference to FIG. 1.

The X-ray imaging apparatus 100 according to Embodiment is configured to take X-ray images respectively with respect to a plurality of strip-shape imaging regions divided along the axial direction (an X-direction) of a subject 10 and to generate an long image employing the axial direction (the X-direction) of the subject 10 as the longitudinal direction by synthesizing the plurality of strip-shape X-ray images.

The X-ray imaging apparatus 100 includes an X-ray tube 1, an FPD (flat panel detector) 2, an imaging platform 3, a real-time synthesis PC (personal computer) 4, a real-time image monitor 5, an image reference/processing PC 6, a diagnostic image monitor 7 and a manual switch 8. The real-time synthesis PC 4 includes a real-time image synthesis element 41. The image reference/processing PC 6 includes an image processing element 61 and a memory 62. The X-ray tube 1 is an example of the "X-ray irradiation element" of the present invention, and the FPD 2 is an example of the "X-ray imaging element" of the present invention. The real-time image monitor 5 is an example of the "first display element" of the present invention, and the diagnostic image monitor 7 is an example of the "second display element" of the present invention. The real-time image synthesis element 41 is an example of the "image synthesis element" of the present invention. The image processing element 61 is an example of the "diagnostic image processing element" of the present invention, and the memory 62 is an example of the "storage element" of the present invention.

The X-ray imaging apparatus 100 is configured to image the subject 10 (a human body) laid down on the imaging platform 3. Specifically, the X-ray imaging apparatus 100 is configured to take an X-ray image by receiving an X-ray irradiated from the X-ray tube 1 arranged above the imaging platform 3 and transmitted through the subject 10 with the FPD 2. Further, the X-ray imaging apparatus 100 is configured to concurrently take a plurality of strip-shape X-ray images while relatively moving the X-ray tube 1 and the FPD 2 with respect to the subject 10. For example, the X-ray imaging apparatus 100 is configured to take X-ray images at the rate of six per one second. The X-ray imaging apparatus 100 is an island-type X-ray imaging apparatus.

Figure 1:
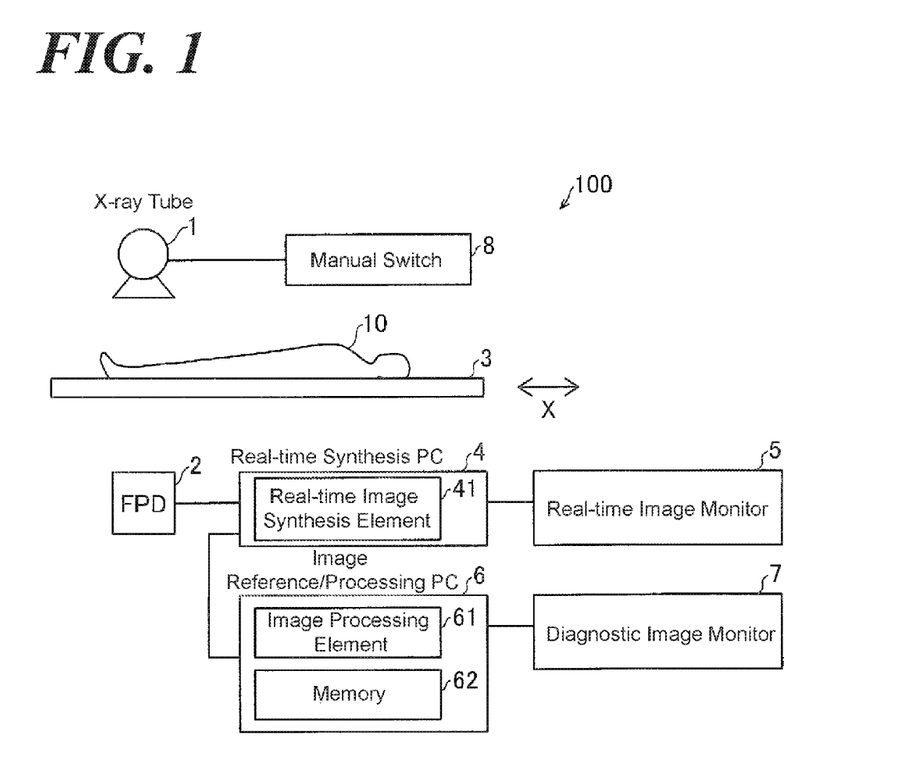
FIG. 1 is a schematic diagram showing the overall structure of an X-ray imaging apparatus according to Embodiment of the present invention.

The X-ray tube 1 is arranged to be opposed to the FPD 2 through the imaging platform 3, as shown in FIG. 1. Further, the X-ray tube 1 irradiates an X-ray to the subject 10 laid down on the imaging platform 3. In addition, the X-ray tube 1 is provided with a mask blocking the X-ray, and so configured that the X-ray is irradiated in a slit manner (in a strip manner) through openings of the mask. In other words, an imaging range of a taken X-ray image is adjusted by adjusting an opening shape of the mask. For example, the width (the length in the X-direction) of an imaged strip is at least 20 mm and not more than 40 mm.

The FPD 2 is configured to take an X-ray image on the basis of the X-ray irradiated by the X-ray tube 1 and transmitted through the subject 10. Further, the FPD 2 is configured to convert the X-ray to an electric signal. Information of the X-ray converted to the electric signal is transmitted to the real-time synthesis PC 4.

The X-ray tube 1 and the FPD 2 are configured to start taking the X-ray image on the basis of an imaging start instruction input from a user (an operator) through the manual switch 8. In other words, the X-ray tube 1 and the FPD 2 are configured to irradiate the X-ray from the X-ray tube 1 and to take the X-ray image by the FPD 2 on the basis of the user's imaging start instruction. Further, the X-ray tube 1 and the FPD 2 are configured to terminate or suspend the imaging of the X-ray image on the basis of an instruction for imaging termination or imaging suspension input from the user through the manual switch 8. In other words, the X-ray tube 1 and the FPD 2 are configured to hold the X-ray irradiation from the X-ray tube 1 and to suspend the imaging of the X-ray image by the FPD 2 on the basis of the user's instruction for imaging termination or imaging suspension.

The imaging platform 3 is configured to be able to relative-move with respect to the X-ray tube 1 and the FPD 2 in a state in which the subject 10 is laid down (placed), as shown in FIG. 1. More specifically, the imaging platform 3 is configured to be movable in the axial direction (the X-direction) of the laid-down subject 10.

According to Embodiment, the real-time synthesis PC 4 is configured to synthesize in turn the plurality of strip-shape X-ray images taken by the FPD 2 every imaging. More specifically, the real-time image synthesis element 41 of the real-time synthesis PC 4 is configured to generate intermediate images 15, 16, 17 and 18 (see FIG. 3) by connecting and synthesizing a plurality of strip-shape X-ray images 11, 12, 13 and 14 (see FIG. 2), concurrently taken in turn while letting the X-ray tube 1 and the FPD 2 relative-move with respect to the subject 10, in this order. Further, the real-time image synthesis element 41 is configured to synthesize a long image of which the longitudinal direction is the X direction from the plurality of strip-shape X-ray images and the short-side direction is the X direction, concurrently taken while letting the X-ray tube 1 and the FPD 2 relative-move with respect to the subject 10.

Figure 2:
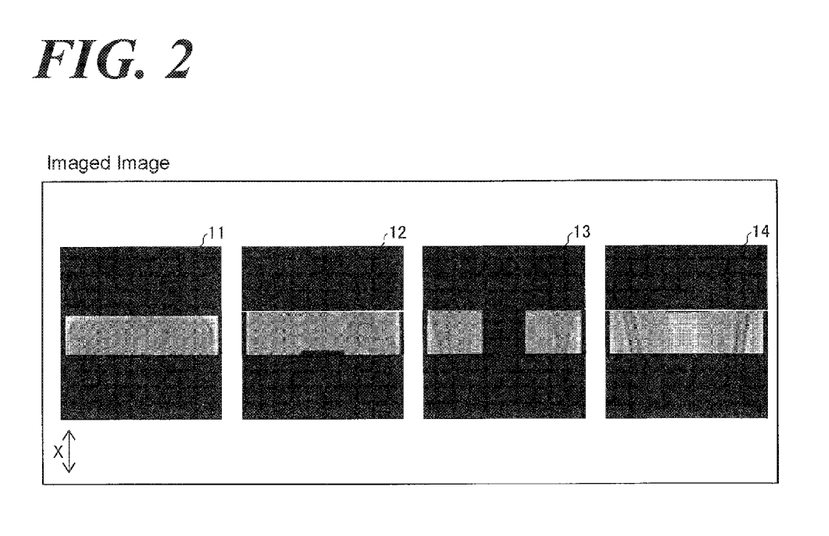
FIG. 2 is a diagram showing strip-shape images taken by the X-ray imaging apparatus according to Embodiment of the present invention.
Figure 3:
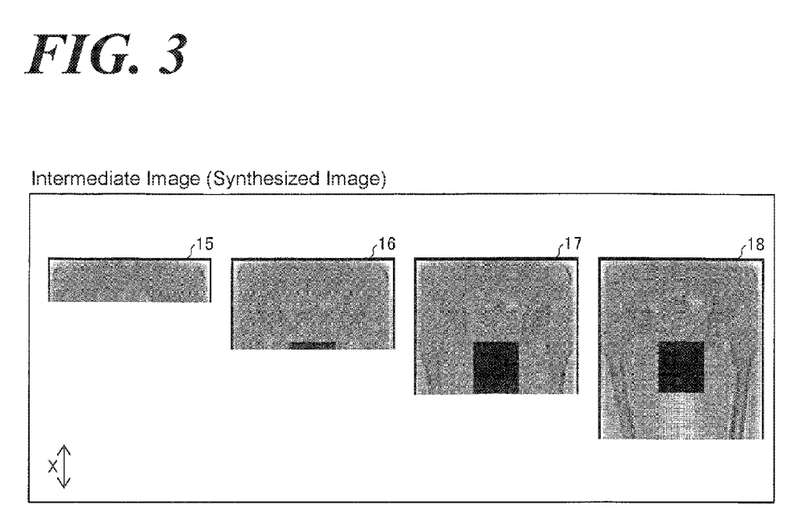
FIG. 3 is a diagram showing intermediate images synthesized by the X-ray imaging apparatus according to Embodiment of the present invention.

In addition, the real-time image synthesis element 41 is configured to obtain the strip-shape X-ray images from images taken by the FPD 2 by cutting both end portions (portions where the X-ray is blocked by the mask) in the X-direction and to synthesize the intermediate images by specifying mutually corresponding portions (overlapping ranges) by image analysis of the obtained plurality of strip-shape X-ray images and connecting the same in the X-direction.

Further, the real-time image synthesis element 41 is configured to generate the intermediate images in a manner updating the same by connecting and synthesizing newly taken strip images to and with the generated intermediate images every imaging. For example, the strip-shape X-ray images 11 and 12 (see FIG. 2) are synthesized, and the intermediate image 16 (see FIG. 3) is generated. Further, the intermediate image 16 (see FIG. 3) and the strip-shape X-ray image 13 (see FIG. 2) are synthesized, and the intermediate image 17 (see FIG. 3) is generated. In addition, the intermediate image 17 (see FIG. 3) and the strip-shape X-ray image 14 (see FIG. 2) are synthesized, and the intermediate image 18 (see FIG. 3) is generated. The intermediate images are generated in turn in the aforementioned manner.

In addition, the real-time image synthesis element 41 is configured to post the user that connected portions deviate on the basis of the synthesized intermediate images in turn, when the connected portions of the synthesized images deviate. Specifically, the real-time image synthesis element 41 is configured to post the user that the connected portions deviate when it is determined that connections of the connected portions are deviated in accordance with performing image analysis of the connected portions (mutually corresponding portions (overlapping ranges) of the plurality of strip-shape X-ray images) of the synthesized images. In addition, a method of posting the user includes steps of displaying by the real-time image monitor 5 and posting with e.g., a sound.

Further, the real-time image synthesis element 41 is configured to display in turn the synthesized intermediate images in turn on the real-time image monitor 5. In addition, the real-time image synthesis element 41 is configured to make the real-time image monitor 5 displaying the intermediate images prior to the time when a next X-ray image is taken. More specifically, the real-time image synthesis element 41 is configured to make the real-time image monitor 5 displaying the intermediate images prior to the time when an X-ray for taking the next X-ray image is irradiated.

Further, the real-time image synthesis element 41 is configured to transmit a synthesized long image to the image reference/processing PC 6 following generating the long image by synthesizing all strip-shape X-ray images.

The real-time image monitor 5 is configured to display the intermediate images taken by the FPD 2 and synthesized in turn by the real-time image synthesis element 41.

The image reference/processing PC 6 is configured to conduct image-processing and store the long image synthesized by the real-time synthesis PC 4. Further, the image reference/processing PC 6 is employed for referring to (browsing) a diagnostic image stored following the image processing.

The image processing element 61 of the image reference/processing PC 6 is configured to perform the image processing for diagnosis with respect to the image synthesized by the real-time image synthesis element 41. Specifically, the image processing element 61 is configured to perform the image processing for diagnosis with respect to the image synthesized by the real-time image synthesis element 41 and temporarily stored in the memory 62. Further, the image processing element 61 is configured to perform the image processing for diagnosis by performing an edge enhancement processing, a pixel correction processing and so forth on the image that have been lengthwise synthesized. In addition, the image processing element 61 is configured to make the diagnostic image monitor 7 displaying the diagnostic image subjected to the image processing for diagnosis and to store the diagnostic image.

The diagnostic image monitor 7 is configured to display the image subjected to the image processing for diagnosis by the image reference/processing PC 6.

The manual switch 8 includes a button, and is configured to perform imaging during push-down of the button and to suspend the imaging when the user releases the button. In other words, the user so operates the manual switch 8 that the imaging is started, while the user so operates the manual switch 8 that the imaging (X-ray irradiation) is suspended, e.g., when synthesized connected portions deviate, following confirming the intermediate images displayed on the real-time image monitor 5.

Figure 4:
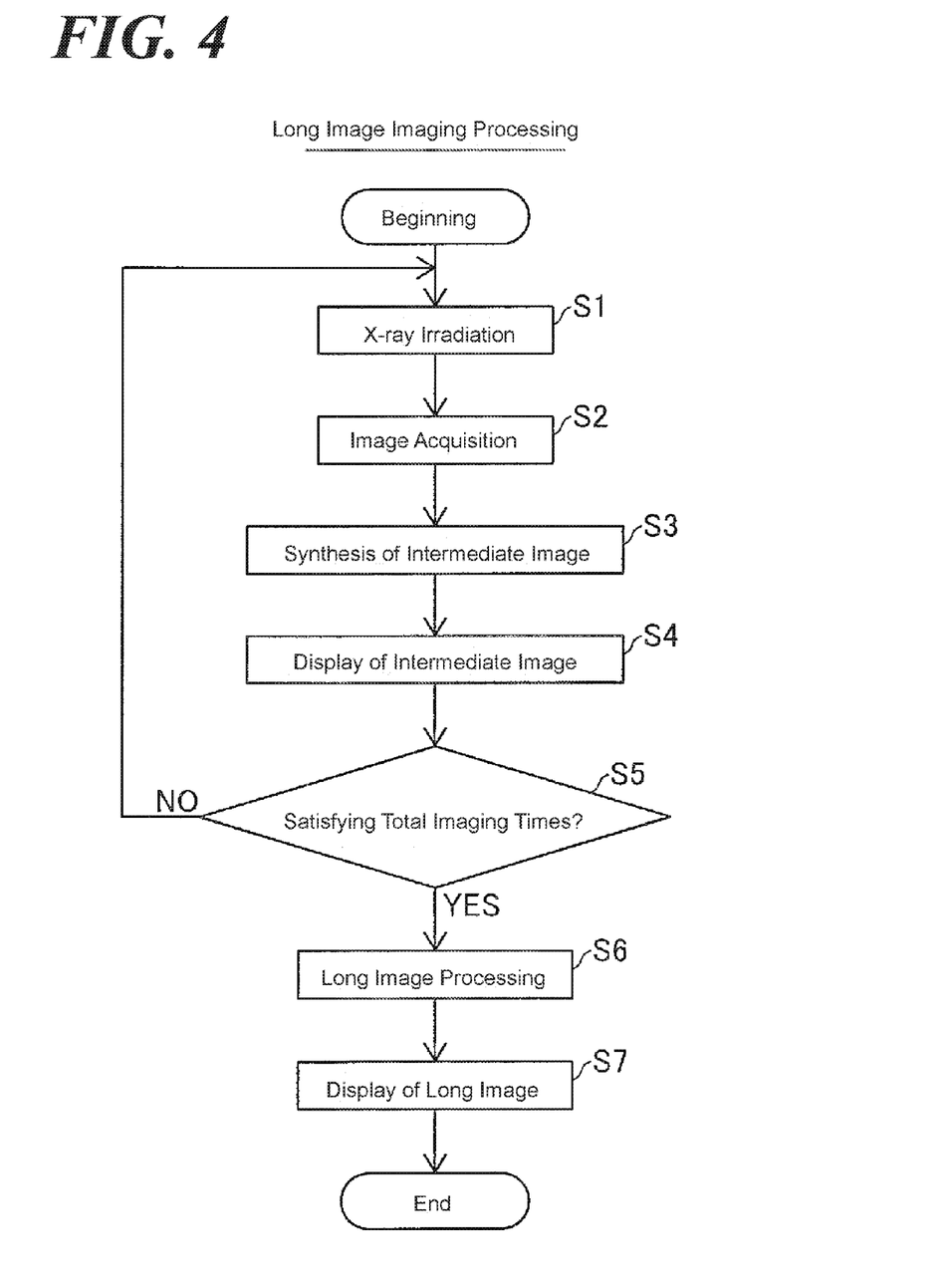
FIG. 4 is a flow chart for illustrating long image taking processing according to Embodiment of the present invention.

A long image taking processing with the X-ray imaging apparatus 100 according to Embodiment is now described with reference to FIG. 4.

When accepting the imaging start instruction from the user through the manual switch 8 after the subject (an imaged person) 10 is laid down (placed) on the imaging platform 3 and an imaging range is set by the user (the operator), an X-ray is irradiated from the X-ray tube 1 at a step S1. Further, a strip-shape X-ray image is taken by the FPD 3. In addition, the imaging platform 3 takes relative-move with respect to the X-ray tube 1 and the FPD 2.

At a step S2, the taken strip-shape X-ray image is acquired by the real-time image synthesis element 41. At a step S3, synthesis of an intermediate image is performed by the real-time image synthesis element 41. In other words, the intermediate image is synthesized every imaging of the strip-shape X-ray image in a successive manner.

At a step S4, the synthesized intermediate image is displayed on the real-time image monitor 5. At a step S5, it is determined whether a total number of imaging times is satisfied or not. In other words, it is determined whether the set imaging range has been imaged or not. If the total number of imaging times is not satisfied, the processing returns to the step S1. If the total number of imaging times is satisfied, the processing advances to a step S6.

At the step S6, image processing of a long image is performed by the image processing element 61. In other words, the whole of the set imaging range is imaged and e.g., edge enhancement and pixel correction are performed with respect to an image lengthwise synthesized by the real-time image synthesis element 41, and then a processing is conducted for a diagnostic image. At a step S7, the long image image-processed for diagnosis is displayed on the diagnostic image monitor 7. Thereafter the long image taking processing is terminated.

According to Embodiment, as hereinabove described, the real-time image synthesis element 41 that synthesizes the image by connecting in turn images of the plurality of strip-shape X-ray images concurrently taken while letting the X-ray tube 1 and the FPD 2 relative-move with respect to the subject 10 and the real-time image monitor 5 displaying the intermediate images taken by the FPD 2 and synthesized in turn by the real-time image synthesis element 41 are so provided that which parts of the subject 10, corresponding to the taken strip-shape X-ray images, can be easily recognized by the intermediate images in which the strip-shape X-ray images between an imaging beginning position and a current imaging position are synthesized. Further, since the images are synthesized halfway through the imaging, not only the deviation can be recognized halfway through the imaging as well, but also the connected portions of the strip-shape X-ray images deviate due to e.g., movement of the subject 10. In this case, since the imaging can be suspended halfway, an increase in X-ray exposure to the subject 10 resulting from a subsequent take can be suppressed.

According to Embodiment, as hereinabove described, the real-time image monitor 5 is configured to display the intermediate images prior to the time when the X-ray for taking the next X-ray image is applied. Thus, the presence or absence of deviation of the connected portions of the X-ray images can be recognized prior to the time of the next take so that an X-ray irradiation for taking the next X-ray image can be suspended by holding the imaging when there is deviation. Thus, the increase in X-ray exposure to the subject 10 can be effectively suppressed.

According to Embodiment, as hereinabove described, the real-time image monitor 5 is configured to display the intermediate images prior to the time when the next X-ray image is taken. Thus, the taken X-ray images can be confirmed in real time by displaying the intermediate images every imaging of the strip-shape X-ray images. Further, the strip-shape X-ray images that have been taken by that time are connected and synthesized prior to the time when the next X-ray image is taken so that a processing burden can be reduced by inhibiting overlapping of an imaging processing timing and a synthesis processing timing.

According to Embodiment, as hereinabove described, the image processing element 61 that performs the image processing for diagnosis with respect to the image synthesized by the real-time image synthesis element 41 and the diagnostic image monitor 7 that displays the image subjected to the image processing for diagnosis are so provided that not only which parts of the subject 10 corresponding to the taken strip-shape X-ray images can be recognized by the intermediate images displayed on the real-time image monitor 5, but also the subject 10 can be diagnosed by the image that is subjected to the image processing for diagnosis and displayed on the diagnostic image monitor 7.

According to Embodiment, as hereinabove described, the image processing element 61 is configured to perform the image processing for diagnosis with respect to the image stored in the memory 62 so that the image processing for diagnosis can be easily performed on the basis of the image that is synthesized by the real-time image synthesis element 41 and stored in the memory 62.

According to Embodiment, as hereinabove described, the real-time image synthesis element 41 is configured to synthesize the long image of which the longitudinal direction is the X-direction from the plurality of strip-shape X-ray images, of which the short-side direction is the X-direction, that are concurrently taken while letting the X-ray tube 1 and the FPD 2 relative-move with respect to the subject 10. Thus, it can be easily recognized by the intermediate images displayed on the real-time image monitor 5 that the plurality of strip-shape X-ray images, of which the short-side direction is the X direction, correspond to which parts of the long image, of which the longitudinal direction is the X direction.

According to Embodiment, as hereinabove described, the real-time image synthesis element 41 is configured to post the user that the connected portions deviate when the connected portions of the synthesized images deviate on the basis of the synthesized intermediate images, in turn. Thus, the user can easily recognize the deviation halfway through the imaging so that the imaging can be suspended by the user, and an operation of retaking with regard to the deviated portions can be easily performed.

The embodiment disclosed this time must be considered as illustrative in all points and not restrictive. The scope of the present invention is specified by the scope of claims but by the above description of Embodiment, and all modifications within the meaning and the scope equivalent to the scope of claims are further included.

For example, while the example in which the subject is the human being has been shown in the aforementioned Embodiment, the present invention is not restricted to the human being. According to the present invention, the subject may be a creature other than the human being, or may be a material. For example, the X-ray imaging apparatus according to the present invention may be employed for a medical apparatus such as a Roentgen apparatus, or may be employed for an industrial instrument such as an X-ray inspection apparatus (a nondestructive inspection device.) Further, the X-ray imaging apparatus according to the present invention may be employed for an analytical instrument and so forth.

While the example of imaging the laid-down subject has been shown in the aforementioned Embodiment, the present invention is not restricted to the present Embodiment. According to the present invention, a subject in a rising state (an upright position) may be imaged.

While the example of the structure in which the image synthesis element of the present invention and the diagnostic image processing element are provided with separate PCs has been shown in the aforementioned Embodiment, the present invention is not restricted to such Embodiment. According to the present invention, the image synthesis element and the diagnostic image processing element may be provided with the same processing apparatus (a personal computer or processing controller (PC), for example).

While the example of the structure in which the real-time image monitor (the first display element) and the diagnostic image monitor (the second display element) are separately provided has been shown in the aforementioned Embodiment, the present invention is not restricted to Embodiment. According to the present invention, the first display element and the second display element may be provided with the same monitor. For example, the same monitor may be partitioned to be employed as the first display element and the second display element.

While the example of the structure of synthesizing the long image from the strip-shape X-ray images has been shown in the aforementioned embodiment, the present invention is not restricted to Embodiment. According to the present invention, it may be a structure of synthesizing a rectangular or square image other than the long one from strip-shape X-ray images.

While the example of connecting in turn and synthesizing the strip-shape X-ray images in real time every time taking the same once has been shown in the aforementioned Embodiment, the present invention is not restricted to Embodiment. According to the present invention, strip-shape X-ray images may be connected and synthesized every two or more imaging times.

While the example of the island-type X-ray imaging apparatus has been shown in the aforementioned Embodiment, the present invention is not restricted to Embodiment. According to the present invention, it may be a C-arm-type X-ray imaging apparatus in which an X-ray irradiation element and an X-ray imaging element are supported by a C-arm.

While the processing of the X-ray imaging apparatus according to the present invention has been illustrated by employing a flow-driven type flow chart performing processing in turn along a processing flow in the aforementioned Embodiment for the convenience of illustration, the present invention is not restricted to Embodiment. According to the present invention, a processing operation may be performed by event driving type (event-driven type) processing executing processing in the units of events. In this case, the processing operation may be performed as a complete event driving type, or may be performed by combining event driving and flow driving.

DESCRIPTION OF REFERENCE SIGNS

1 X-ray tube (X-ray irradiation element)
2 FPD (X-ray imaging element)
5 Real-time image monitor (first display element)
7 Diagnostic image monitor (second display element)
10 Subject
41 Real-time image synthesis element (image synthesis element)
61 Image processing element (diagnostic image processing element)
62 Memory (storage element)
100 X-ray imaging apparatus

What is claimed is:
1. An X-ray imaging apparatus, comprising:
an X-ray irradiation element that irradiates an X-ray to an external subject;
an X-ray imaging element that operatively takes an X-ray image on the basis of the X-ray transmitted through said subject;
an image synthesis element that is operative to receive and synthesize an image by connecting in turn a plurality of strip-shape X-ray images concurrently taken while letting said X-ray irradiation element and said X-ray imaging element concurrently move along a path relative to said subject; and a first display element that displays an intermediate image imaged by said X-ray imaging element and which is successively synthesized in turn by said image synthesis element.

2. The X-ray imaging apparatus, according to claim 1, wherein:
said first display element is configured to display said intermediate image prior to the time when an X-ray for taking a next X-ray image is irradiated.

3. The X-ray imaging apparatus, according to claim 1, wherein:
said first display element is configured to display said intermediate image prior to the time when a next X-ray image is imaged.

4. The X-ray imaging apparatus, according to claim 1, further comprising:
a diagnostic image processing element that performs an image processing for diagnosis with respect to the image synthesized by said image synthesis element, and
a second display element that displays the image subjected to the image processing for diagnosis.

5. The X-ray imaging apparatus, according to claim 4, further comprising:
a storage element that successively stores the images synthesized by said image synthesis element, and
wherein said diagnostic image processing element is configured to perform the image processing for a diagnosis with respect to the image stored in said storage element.

6. The X-ray imaging apparatus, according to claim 4, wherein:
said image synthesis element is configured to operatively synthesize a long image of the plurality of said strip-shape X-ray images, of which a longitudinal direction is defined relative to a predetermined direction, and of which a short-side direction is defined orthogonal to said predetermined direction, and to concurrently synthesize said strip-shaped X-ray images taken while letting said X-ray irradiation element and said X-ray imaging element move relative with respect to said subject in said predetermined direction.

7. The X-ray imaging apparatus, according to claim 1, wherein:
said image synthesis element is further operatively configured to generate a notice to a user when the connected portion of the synthesized images deviates on the basis of the successively synthesized intermediate image in turn.

8. A method for X-ray imaging, comprising the steps of:
irradiating an X-ray to an external subject;
taking an X-ray image on a basis of the X-ray transmitted through said subject;
synthesizing an image by connecting in turn an image of a plurality strip-shape X-ray images concurrently taken while letting an X-ray irradiation element and an X-ray imaging element move relative with respect to said subject; and
concurrently displaying an intermediate image synthesized, by connecting in turn a plurality of successively composed intermediate images from said X-ray imaging element on a first display element.

9. The X-ray imaging method, according to claim 8, wherein:
the step of displaying said intermediate image on the display element further includes a step of displaying said intermediate image synthesized in turn prior to the time when an X-ray for taking a next X-ray image is next irradiated.

10. The X-ray imaging method, according to claim 8, wherein:
the step of displaying said intermediate image on the display element further includes a step of displaying the successive intermediate image synthesized in turn prior to the time when a next X-ray image is taken.

11. The X-ray imaging method, according to claim 8, further comprising the steps of:
a step of performing an image processing for diagnosis with respect to the synthesized image, and
a step of displaying the image subjected to the image processing for diagnosis on a second display element.

* * * * *